United States Patent
Heidt et al.

(12) 
(10) Patent No.: US 6,313,340 B1
(45) Date of Patent: Nov. 6, 2001

(54) PROCESS FOR THE PREPARATION OF METHYL P-VINYLBENZOATE AND P-VINYL BENZOIC ACID, AND THEIR USE IN LATEX COMPOSITIONS

(75) Inventors: Philip Conrad Heidt, Kingsport; Matthew Lynn Elliott, Mount Carmel; Mahendra Kumar Sharma, Kingsport, all of TN (US)

(73) Assignee: Eastman Chemical Corporation, Kingsport, TN (US)

( * ) Notice: Subject to any disclaimer, the term of this patent is extended or adjusted under 35 U.S.C. 154(b) by 0 days.

(21) Appl. No.: 09/358,776

(22) Filed: Jul. 22, 1999

Related U.S. Application Data

(60) Provisional application No. 60/112,398, filed on Dec. 15, 1998.

(51) Int. Cl.$^7$ .................................................. C07C 69/76
(52) U.S. Cl. ............................................ 560/51; 560/104
(58) Field of Search ........................................ 560/51, 104

(56) References Cited

U.S. PATENT DOCUMENTS

| | | |
|---|---|---|
| 4,609,756 | 9/1986 | Dorlars et al. . |
| 4,935,559 | 6/1990 | Rule et al. . |

FOREIGN PATENT DOCUMENTS

| | | |
|---|---|---|
| 636196 | 4/1950 | (GB) . |

OTHER PUBLICATIONS

Hurd, Charles et al, "The Interaction of Ketene with Aromatic Aldehydes and its Bearing on the Perkin Reaction", Journal of the American Chemical Society, vol. 55, No. 1, Jan. 1933, pp. 275–283.
Aldrich Catalog Handbook of Fine Chemicals, 1996–97.*
Morrison and Boyd, Organic Chemistry, fifth Edition, 1987.*
Tetrahedron, vol. 52, No. 3, pp. 915–924, 1996, "Olefination and Hydroxymethylation of Aldehydes Using Knochel's (Dialkoxyboryl)methylcopper Reagents," Sakai et al.
Journal of Molecular Catalysis A: Chemical 97 (1995), pp. 73–77, "Palladium–catalyzed, Arylation of Ethyene (The Heck Reaction) Under Aqueous Conditions," Kiji et al.
Chemistry and Industry, Mar. 20, 1989, p. 192, "Palladium–Catalysed Arylationof Ethylene with Arylsulphonyl Chlorides," Kasahara et al.
Bulletin of the Chemical Society of Japan, vol. 52 (9), pp. 2609–2610, (1979), "Reaction of Diazonium Salts with Transition Metals. II. Palladium–catalyzed Arylation of Ethylene with Arenediazaonium Salts," Kikikawa et al.
J. Am. Chem. Soc., 68, 674, 1946, "The Use of Liquid Phase Oxidation for the Preparation of Nuclearly Substituted Styrenes. I. Methyl p–Vinylbenzoate," Emerson et al.
J. Org. Chem., 24, 549, 1959, "p–Vinylbenzoic and p–Vinylphenylacetic Acids," Bergmann et al.
J. Am. Chem. Soc, 67, 2250, 1945, "Preparation and Polymerization of p–Cyanostyrene, p–Vinylbenzoic Acid and its Methyl Ester," Marvel et al.
J. Am Chem. Soc., 67, 2250, 1945, "The Interaction of Ketene with Aromatic Aldehydes and its Bearing on the Perkin Reaction," Hurd et al.
PhD Thesis, Cornell University, 1933, "Reactions of Ketene with Aromatic Aldehydes: The Perkin Reaction The Structure of Butadiene Oxide," Paul Wendell Vittum pp. 23–27 missing.

* cited by examiner

*Primary Examiner*—Gary Geist
*Assistant Examiner*—Hector M Reyes
(74) *Attorney, Agent, or Firm*—Matthew Smith, Esq.; Harry J. Gwinnell

(57) ABSTRACT

The present invention describes a process for the direct preparation of methyl p-vinylbenzoate from methyl p-formylbenzoate using ketene in the presence of potassium acetate. The chief products obtained from the process are about a five to two ratio of methyl p-vinylbenzoate to p-carbomethoxycinnamic acid. The latter may be thermally decarboxylated, especially in the presence of copper powder, to produce additional quantities of methyl p-vinylbenzoate. Methyl p-vinylbenzoate may further undergo hydrolysis to form p-vinyl benzoic acid. Both methyl p-vinyl benzoate and p-vinyl benzoic acid may be polymerized with ethylenically unsaturated monomers to form useful latex compositions of the present invention.

14 Claims, No Drawings

PROCESS FOR THE PREPARATION OF METHYL P-VINYLBENZOATE AND P-VINYL BENZOIC ACID, AND THEIR USE IN LATEX COMPOSITIONS

CROSS REFERENCE TO RELATED APPLICATIONS

This application claims the benefit of U.S. Provisional Application No. 60/112,398 filed on Dec. 15, 1998.

BACKGROUND OF THE INVENTION

Methyl p-vinylbenzoate has been prepared from a number of different synthetic pathways over the years including the most direct route, esterification of p-vinylbenzoic acid itself. However, even with the direct esterification route itself, one must first prepare the p-vinylbenzoic acid which can involve a number of synthetic sequences in itself. Thus, a number of approaches have been developed which produce methyl p-vinylbenzoate without going through the acid first.

The most direct olefination route prior to this invention involved reacting methyl p-formylbenzoate under boron-Wittig like conditions as is described by Saki, et al in Tetrahedron, 52(3), 915, 1996. However, the use of Knochel's borylmethylcopper reagent does not lend itself for large-scale industrial reactions nor is it economical for producing such quantities.

Several olefination routes based on Heck and Heck-related arylation of ethylene have been reported. One such method involving the palladium catalyzed arylation of ethylene with methyl p-bromobenzoate has been described by J. Kiji, et al in J. Mol. Cat. A: *Chem.* 97, 73, 1995. A reaction involving methyl p-iodobenzoate has been described by Rule and Fugate in U.S. Pat. No. 4,935,559 (assigned to Eastman Kodak). Both of the latter reactions involve the use of halogenated compounds which one must address environmental concerns. Other related chemistries involve methyl p-chlorosulfonylbenzoate as described by Kasahara, et al in Chem. Ind., 6, 192, 1989 and arenediazonium salts as described by Kikukawa, et al in Bull. Chem. Soc. Jpn., 52(9), 2609, 1979.

Still, other routes involve the oxidation of methyl p-ethylbenzoate to either methyl p-acetylbenzoate first as in British patent 636,196 (assigned to Monsanto Chemical Company) and by Emerson, et al in J. Am. Chem. Soc., 68, 674, 1946 or to the methyl p-alpha-hydroxyethylbenzoate via the bromo-derivative as described by Bergmann and Blum in J. Org. Chem., 24, 549, 1959. Although these routes could produce large-quantities of methyl p-vinylbenzoate, they too have several synthetic steps not mentioned which adds to the cost of production.

Methyl p-vinylbenzoate has been prepared by several groups of individuals which is more suited to academic and smaller research laboratories. These processes include p-methylacetophenone described by Bergmann and Blum, or through either p-cyanoacetophenone or p-dibromobenzene, both described by Marvel and Overberger in J. Am. Chem. Soc., 67, 2250,1945.

The process of direct olefination of an aromatic aldehyde with ketene in the presence of a potassium salt has been described previously by Hurd and Thomas in J. Am. Chem. Soc., 55, 275, 1933 and by Vittum in his PhD Thesis, Cornell University, 1933. The most detailed work describing this olefination which in many ways resembles the Perkin reaction has been described by Vittum. Most reactions were carried out using benzaldehyde with ketene and some type of "catalyst" to prepare styrene and cinnamic acid, the primary reaction products from this reaction. It has been found that temperature variations over a relatively wide range have little impact on the yields and ratios of styrene and cinnamic acid. Additionally, a salt is needed in the course of the reaction and in particular, potassium salts are preferred.

Prior studies involving substituted aromatic aldehydes such as meta-and para-nitrobenzaldehyde, and anisaldehyde (para-methoxybenzaldehyde) suggest that direct olefination of the aldehyde group with ketene is not very feasible. In these cases, no reaction products of meta- or para-nitrovinylbenzene (meta-or para-nitrostyrene) or para-methoxyvinyl-benzene (para-methoxystyrene) was produced and only in the case of meta-nitrobenzaldehyde were any of the corresponding cinnamic acid derivatives isolated. In particular, the starting aldehyde is generally recovered or a tarry residue formed in addition to the recovered starting aldehyde. Most substituted aldehydes in the Perkin reaction, especially those substituted in the para position have a large negative influence on the rate of reaction. Additionally, the type of substituent can have a large influence on the reactivity of the aldehyde in the Perkin reaction.

Thus, the need exists for a process for preparation of methyl p-vinylbenzoate from the reaction of methyl p-formylbenzoate with a ketene in the presence of a potassium salt. The present invention provides such a process.

BRIEF SUMMARY OF THE INVENTION

The present invention describes a direct method for preparation of methyl p-vinylbenzoate by the reaction of methyl p-formylbenzoate with ketene in the presence of a potassium salt. The present method has the advantage of large-scale economical production of methyl p-vinylbenzoate. It is both unexpected and unobvious that methyl p-formylbenzoate with its para methyl ester substituent would even react with ketene in the presence of a potassium salt to form methyl p-vinylbenzoate, based on prior work by others as discussed above.

The above reaction also yields p-carbomethoxycinnamic acid as a coproduct with methyl p-vinylbenzoate. It has also been discovered that additional quantities of methyl p-vinylbenzoate may be prepared by thermal decarboxylation of p-carbomethoxycinnamic acid in the presence of copper powder. Methyl p-vinylbenzoate may be further reacted by hydrolysis to form p-vinyl benzoic acid.

Both methyl p-vinylbenzoate and p-vinyl benzoic acid have been found to be useful monomers for emulsion polymerization with other ethylenically unsaturated monomers to form latex compositions. Both the latex compositions and the monomers of the present invention may be used in a number of end-use applications, such as coatings, photoresists, and as a partial replacement of styrene in unsaturated polyesters.

DETAILED DESCRIPTION OF THE INVENTION

Applicants have discovered processes for the preparation of methyl p-vinylbenzoate (MVB) from methyl p-formylbenzoate. More specifically, methyl p-formylbenzoate reacts with ketene in the presence of a potassium salt, such as potassium acetate, to form methyl p-vinylbenzoate and p-carbomethoxycinnamic acid.

The source of ketene generation used may be from the pyrolysis of acetone; however, any other method of ketene generation known in the art may be used. Ketene may also be obtained by pyrolysis of, for example, diketene, acetic anhydride, and acetic acid. The relative amount of ketene to methyl p-formylbenzoate used may vary from less than 10 percent to more than 500 percent depending on conditions used, desired conversion rates, and desired selectivity.

Suitable potassium salts for initiation of the reaction include, but are not limited to potassium acetate, potassium carbonate, potassium benzoate, potassium cinnamate, and potassium proprionate. When an equivalent of potassium salt is used, based on the aldehyde, almost no styrene is produced; while 15–20 percent of p-carbomethoxycinnamic acid is produced.

The level of potassium salt used may vary from less than one mole percent to more than 100 mole percent based on methyl p-formylbenzoate. It is preferred that the molar ratio of potassium salt to methyl p-formylbenzoate be less that 0.50. It is even more preferred that the molar ratio of potassium salt to methyl p-formylbenzoate be less than 0.20.

At low temperatures, it may be necessary to dissolve the methyl p-formylbenzoate in a suitable solvent. Useful solvents for the reaction include aliphatic and cycloaliphatic hydrocarbons; aromatic hydrocarbons; cyclic and acyclic ethers, esters and ketones. The amount of solven may be as much as necessary to make up to a 0.001 molar solution. Preferably, the methyl p-formylbenzoate is dissolved in enough solven to make a 0.1 to 10.0 molar solution. At higher temperatures, solvents may not be necessary to carry out the reaction.

In general terms, the process of the present invention involves reacting a mixture of an aromatic aldehyde and potassium salt with ketene. More specifically, the aromatic aldehyde is methyl p-formylbenzoate. The mixture of aromatic aldehyde and potassium salt is generally heterogeneous, unless a particular potassium salt is soluble in methyl p-formylbenzoate, in which case it would be homogeneous. At lower temperatures, methyl p-formylbenzoate is a solid so it is preferable to add a solvent prior to adding the potassium salt. The ketene may be bubbled into the reaction vessel as a gas, or may be condensed first and added as a liquid. The reaction may be carried out at temperatures ranging from about 0° C. to about 200° C., though it is preferable to be between about 20° C. and about 80° C. at low pressures (up to 5 atmospheres). The pressure of reaction may be from less than one atmosphere to more than 100 atmospheres using appropriate autoclave equipment to withstand the higher pressures. Since methyl p-formylbenzoate melts at about 62° C., reactions carried out above these temperature may be carried out without addition of solvents. Generally, as the reaction temperature increases, the reaction time is shortened to reduce potential polymerization of the desired product(s). Suitable reaction times are generally up to about 100 hours at temperatures up to about 30° C. At temperatures greater than 40° C., an antioxidant and/or polymerization inhibitor may be added at concentrations up to about five percent. Suitable antioxidants include, but are not limited to, hydroquinone, t-butyl hydroquinone, hindered phenols, hydroquinone ethoxyethers, and butylated hydroxytoluene.

The main products obtained from the process of the present invention are about a five to two ratio of methyl p-vinylbenzoate to p-carbomethoxycinnamic acid. The latter may also be subjected to thermal decarboxylation, in the presence of copper powder, to produce additional quantities of methyl p-vinylbenzoate, using known decarboxylation conditions. Suitable decarboxylation conditions include, but are not limited to, temperatures ranging from about 150° C. to about 350° C.; pressures of up to about 100 atmospheres; and times up to about 24 hours. In addition, the process may be carried out in the presence of an antioxidant or other polymerization inhibitor as described above.

Another embodiment of the present invention is a process for the preparation of p-vinyl benzoic acid by reacting methyl p-formylbenzoate and ketene, in the presence of a potassium salt, to form methyl p-vinylbenzoate; followed by hydrolysis of methyl p-vinylbenzoate to p-vinyl benzoic acid.

The hydrolysis of esters may typically be catalyzed by an acid or a base. When hydrolysis of esters occur under basic conditions such as sodium hydroxide, the hydrolysis is referred to as saponification. Saponification provides the salt of the carboxylic acid which may then be further reacted with an acid, such as a mineral acid, to provide the carboxylic acid.

The hydrolysis of methyl p-vinylbenzoate (MVB) to p-vinylbenzoic acid (VBA) may occur by the saponification of methyl p-vinylbenzoate with aqueous sodium hydroxide, separation from organic impurities by phase separation, followed by the addition of aqueous hydrochloric acid to provide p-vinylbenzoic acid (VBA).

Methyl p-vinyl benzoate (MVB) and p-vinyl benzoic acid (VBA) of the present invention may be used as monomers in a free radical emulsion polymerization to form latex polymers, using conventional emulsion polymerization techniques. Other monomers that may be used in combination with the monomers of the present invention to form the latex polymers may be broadly characterized as ethylenically unsaturated monomers. These include, but are not limited to, non-acid vinyl monomers, acid vinyl monomers and/or mixtures thereof. The latex polymers of the invention may be copolymers of non-acid vinyl monomers and acid monomers, mixtures thereof and their derivatives. The latex polymers of the invention may also be homopolymers of ethylenically unsaturated monomers.

Suitable non-acid vinyl monomers that may be used to prepare the latex polymer include, but are not limited to, acetoacetoxy ethyl methacrylate, acetoacetoxy ethyl acrylate, methyl acrylate, methyl methacrylate, ethyl acrylate, ethyl methacrylate, butyl acrylate, butyl methacrylate, isobutyl acrylate, isobutyl methacrylate, ethylhexyl acrylate, 2-ethylhexyl methacrylate, 2-ethyl hexyl acrylate, isoprene, octyl acrylate, octyl methacrylate, iso-octyl acrylate, iso-octyl methacrylate, trimethyolpropyl triacrylate, styrene, α-methyl styrene, glycidyl methacrylate, carbodiimide methacrylate, $C_1$–$C_{18}$ alkyl crotonates, di-n-butyl maleate, α or-β-vinyl naphthalene, di-octylmaleate, allyl methacrylate, diallyl maleate, di-allylmalonate, methoxybutenyl methacrylate, isobornyl methacrylate, hydroxybutenyl methacrylate, hydroxyethyl (meth)acrylate, hydroxypropyl(meth)acrylate, acrylonitrile, vinyl chloride, vinylidene chloride, vinyl acetate, vinyl ethylene carbonate, epoxy butene, 3,4-dihydroxybutene, hydroxyethyl(meth)acrylate, methacrylamide, acrylamide, butyl acrylamide, ethyl acrylamide, butadiene, vinyl ester monomers, vinyl(meth)acrylates, isopropenyl(meth) acrylate, cycloaliphatic epoxy(meth)acrylates, ethylformamide, 4-vinyl-1,3-dioxolan-2-one, 2,2-dimethyl-4 vinyl-1,3-dioxolane, and 3,4-di-acetoxy-1-butene or a mixture thereof. Suitable non-acid vinyl monomers are described in The Brandon Associates, 2nd edition, 1992 Merrimack, N.H., and in *Polymers and Monomers*, the 1966–1997 Catalog from Polyscience, Inc., Warrington, Pa., U.S.A.

Acid vinyl monomers that may be used to prepare the latex polymer include, but are not limited to, acrylic acid, methacrylic acid, itaconic acid, crotonic acid, monovinyl adipate, and mixtures thereof.

Preferred monomers useful for making the latex polymers/(co) polymers are ethylenically unsaturated monomers including, but not limited to, acrylates, methacrylates, vinylesters, styrene, styrene derivatives, vinyl chloride, vinylidene chloride, acrylonitrile, isoprene and butadiene. In a more preferred embodiment, the latex polymer comprises (co)polymers made from monomers of 2-ethyl-hexyl acrylate, styrene, butylacrylate, butylmethacrylate, ethylacrylate, methylmethacrylate, butadiene and isoprene.

In a preferred embodiment, the latex polymer of the present invention has a weight average molecular weight (Mw) range of from about 10,000 to about 2,000,000 as determined by gel permeation chromatography (GPC); more preferably the weight average molecular weight range is from about 50,000 to about 1,000,000.

In one embodiment, the glass transition temperature (Tg) of the latex polymer is in the range of from about –50° C. to about 150° C.

The latex compositions of the present invention may be characterized as stabilized latexes in a continuous phase by addition of a diol component. A stable latex is defined for the purposes of this invention as one in which the particles are colloidally stable, i.e., the latex particles remain dispersed in the continuous phase for long periods of time, such as 24 hours, preferably 48 hours, weeks even more preferably, several months.

The latex polymer particles generally have a spherical shape and may be a core shell polymer or a non core-shell polymer. When a core shell polymer is utilized, the polymers may be prepared in a core/shell fashion by staging the monomer addition. For example, the composition of the monomer feed of the polymerization may be changed over the course of the reaction in an abrupt fashion, resulting in a distinct core and shell portion to the polymer.

Preferred monomers useful for making core-shell latex polymers/(co)polymer are ethylenically unsaturated monomers including, but not limited to, acrylates, methacrylates, vinylesters, styrene, styrene derivatives, vinyl chloride, vinylidene chloride, acrylonitrile, isoprene and butadiene. In a more preferred embodiment, the core-shell latex polymer comprises (co)polymers made from monomers of 2-ethyl-hexyl acrylate, styrene, butylacrylate, butylmethacrylate, ethylacrylate, methylmethacrylate, butadiene and isoprene.

The core/shell polymer particles may also be prepared in a multi-layer form, a peanut shell, an acorn form, or a raspberry form. In these type particles, the core portion may comprise from about 20 to about 80 percent of the total weight of the particle and the shell portion may comprise from about 80 to about 20 percent of the total weight volume of the particle.

In one preferred embodiment, chain transfer agents may be used in the emulsion polymerization. Typical chain transfer agents are those known in the art. Chain transfer agents that may be used in the emulsion polymerization reaction to form the diol latex compositions include, but are not limited to, butyl mercaptan, dodecyl mercaptan, mercaptopropionic acid, 2-ethylhexyl-3-mercaptopropionate, n-butyl-3-mercaptopropionate, octyl mercaptan, isodecyl mercaptan, octadecyl mercaptan, mercaptoacetate, allyl mercaptopropionate, allyl mercaptoacetate, crotyl mercaptoproprionate, crotyl mercaptoacetate, and the reactive chain transfer agents disclosed or described in U.S. Pat. No. 5,247,040, incorporated herein by this reference. Preferably the chain transfer agent is selected from mercaptans and various alkyl halides, including but not limited to carbon tetrachloride; more preferably the chain transfer agent is 2-ethylhexyl-3-mercaptopropionate. Chain transfer agents may be added in amounts from 0 to 2 parts per hundred monomer (phm), more preferably 0 to 0.5 phm.

Latex polymers of the invention may be uncrosslinked or crosslinked. When crosslinked, suitable crosslinking agents include multifunctional unsaturated compounds including, but not limited to, divinyl benzene, allyl methacrylate, allyl acrylate, multifunctional acrylates and mixtures thereof. Suitable multifunctional acrylates include, but are not limited to, ethylene diol dimethacrylate, ethylene diol diacrylate, trimethylolpropane triacrylate, trimethylolpropane trimethacrylate, pentaerythritoltetraacrylate and mixtures thereof. The amount of crosslinking monomer in the emulsion polymerization may be controlled to vary the gel fraction of the latex from about 20 to about 100 percent. The gel fraction is the amount that will not dissolve in a good solvent.

The latex particles may be functionalized by including monomers with pendent functional groups. Functional groups that may be incorporated in the latex particle include, but are not limited to, epoxy groups, acetoacetoxy groups, carbonate groups, hydroxyl groups, amine groups, isocyanate groups, amide groups, and mixtures thereof. The functional groups may be derived from a variety of monomers, including, but not limited to, glycidyl methacrylate, acetoacetoxy ethyl methacrylate, vinyl ethylene carbonate, hydroxyl ethyl methacrylate, t-butylaminoethyl methacrylate, dimethylamino methacrylate, m-isopropenyl-alpha,alphadimethylbenzyl isocyanate, acrylamide and n-methylolacrylamide. The addition of functional groups allows for further reaction of the polymer after latex synthesis.

Initiators may also be used in the emulsion polymerization to form the latex compositions, which include, but are not limited to salts of persulfates, water soluble organic peroxides and azo type initiators. Preferred initiators include, but are not limited to hydrogen peroxide, potassium or ammonium peroxydisulfate, dibenzoyl peroxide, lauryl peroxide, ditertiary butyl peroxide, 2,2'-azobisisobutyronitrile, t-butyl hydroperoxide, benzoyl peroxide, and mixtures thereof. Redox initiation systems (Reduction Oxidation Initiation) such as iron catalyzed reaction of t-butyl hydroperoxide with isoascorbic acid are also useful. It is preferable not to use initiators capable of generating a strong acid as a by-product. This prevents possible side reactions of the diol component of the solvent with the acid. Initiators may be added in amounts from 0.1 to 2 phm, more preferably from 0.3 to 0.8 phm.

Reducing agents may also be used in the emulsion polymerization. Suitable reducing agents are those that increase the rate of polymerization include, for example, sodium bisulfite, sodium hydrosulfite, sodium formaldehyde sulfoxylate, ascorbic acid, isoascorbic acid and mixtures thereof. If a reducing agent is introduced into the emulsion polymerization, it is preferably added in an amount of 0.1 to 2 phm, more preferably 0.3 to 0.8 phm. It is preferable to feed the reducing agent into the reactor over a period of time.

Buffering agents may also be used in the emulsion polymerization to control the pH of the reaction. Suitable buffering agents include, but are not limited to, ammonium and sodium salts of carbonates and bicarbonates. It is preferred that the buffering agents be included when using acid generating initiators, including, but not limited to, the salts of persulfates.

Polymerization catalysts may also be used in the emulsion polymerization. Polymerization catalysts are those compounds that increase the rate of polymerization and which, in combination with the above described reducing agents, may promote decomposition of the polymerization initiator under the reaction conditions. Suitable catalysts include, but are not limited to, transition metal compounds such as, for example, ferrous sulfate heptahydrate, ferrous chloride, cupric sulfate, cupric chloride, cobalt acetate, cobaltous sulfate, and mixtures thereof.

This invention may be further illustrated by the following examples of preferred embodiments thereof, although it will be understood that these examples are included merely for purposes of illustration and are not intended to limit the scope of the invention unless otherwise specifically indicated.

EXAMPLES

The materials and testing procedures used for the results shown herein are as follows:

Molecular weight distributions were determined by gel permeation chromatography (GPC). Solutions were made by dissolving about 4 mg of polymer in a 30/70 by weight solution of hexafluoroisopropanol/methylene chloride containing 10% by volume toluene as a flow rate marker. The system was calibrated using a series of narrow molecular weight polystyrene standards. The molecular weights were reported in absolute molecular weight values determined from a set of Mark-Houwink constants that relate PET to polystyrene.

Thermal transitions were determined by differential scanning calorimetry (DSC) on a DuPont instruments 2200 DSC. The DSC experiments were performed using a scan rate of 20° C./minute after the sample was heated above its melting temperature and rapidly quenched below its glass transition temperature.

The particle size of the polymer latex dispersions was measured by light scattering method using Ultra Particle Analyzer (UPA) called Microtrac from Leeds and Northrup Instruments.

Example 1

Preparation of Methyl p-Vinylbenzoate (MVB)

To a three-neck, round-bottom flask equipped with an overhead stirrer, addition funnel, and a nitrogen inlet was added sodium hydride as a 60 percent dispersion (58.5 g, 1.46 mole). The sodium hydride was washed with THF (300 mL) then fresh THF (2000 mL) added. To the well-stirred suspension at room temperature was added methyltriphenylphosphonium bromide (500.1 g, 1.40 mole) over 35 minutes. After another 40 minutes of stirring, a solution of methyl p-formylbenzoate (218.9 g, 1.33 mole) in THF (600 mL) was added over 20–25 minutes. The mixture was then stirred at room temperature overnight for a total of 18 hours. The mixture was then filtered and the filtrate concentrated in vacuo. The residue was then treated with a 50 percent solution of ethyl acetate in hexanes (1400 mL) and filtered again. This filtrate was then concentrated in vacuo and placed on a large chromatography column (1400 mL of silica gel 60, 35–70 mesh packed with a 5 percent solution of ethyl acetate in hexanes) and eluted with a 5 percent solution of ethyl acetate in hexanes. The desired fractions were combined and concentrated in vacuo to provide 180.67 g (83.5 percent) of oil which slowly solidified to a white waxy solid. Proton NMR (Gemini 300 MHz in deuterochloroform): delta 7.98 (2H), 7.42 (2H), 6.72 (1H), 5.82 (1H), 5.37 (1H), 3.88 (3H). FDMS confirmed a mass of 162.

Example 2

Preparation of Methyl p-Vinylbenzoate (MVB)

Acetone (1250 mL) was charged to a 2-L round-bottom flask through an addition funnel as shown in FIG. 1. To a separate 2-L, 3-neck round-bottom flask equipped with a magnetic stirring bar was charged, methyl p-formylbenzoate (164.16 g, 1.0 mole), potassium acetate (9.82 g, 0.10 mole), and THF (500 mL). To a 1-L, 3-neck round-bottom flask was charged methanol (700 mL) for use as a scrubber for unreacted ketene which might pass through the reaction flask. Once all of the flasks were charged, the complete system was flushed with nitrogen for several hours before the flask containing the acetone was heated to a gentle reflux. Once the system was believed to be completely purged of air, the metal filament was heated to a dull-red color (ketene generator set-up is available from Ace Glass while all the other equipment needed is available from both Ace Glass and Lab Glass) and the ketene generated (conversion not determined) bubbled into the reaction flask.

A potential hazard may exists if the bubbler tube in the reaction flask is inserted into the reaction mixture before ketene is generated. The solid potassium salt in the reaction flask may plug the tube creating pressure from the ketene generator to the reaction flask. Thus, ketene is first generated creating a positive pressure in the line, then the bubbler tube may be inserted into the reaction mixture.

Acetone was continued to be pyrolyzed until a sufficient conversion of the methyl p-formylbenzoate was observed. Approximately 10 hours of acetone pyrolysis was required to achieve a conversion of 85 percent of the methyl p-formylbenzoate with a selectivity of 67 percent to methyl p-vinylbenzoate and about 26 percent to what was believed to be p-carbomethoxycinnamic acid as determined by its retention time in the gas chromatograph to a sample of p-carbomethoxycinnamic acid prepared an alternative way.

A sample of the mixture prepared above was vacuum distilled into four fractions. Each of the four fractions contained methyl p-vinylbenzoate and the latter two fractions contained some unreacted methyl p-formylbenzoate. Of the 72.6 g of distillate recovered, 58.3 g were methyl p-vinylbenzoate and 6.8 g was methyl p-formylbenzoate.

Example 3

Preparation of p-Vinylbenzoic Acid (VBA)

To a well-stirred solution of methyl p-vinylbenzoate (36.0 g, 0.222 mole) in THF (200 mL) was added a solution of sodium hydroxide (17.78 g, 0.444 mole) in water (200 mL) at room temperature. After stirring overnight, water (100 mL), THF (150 mL), and ethyl ether (200 mL) was added and the phases separated. The aqueous phase was acidified with a solution of concentrated hydrochloric acid (41 mL) in water (90 mL) then extracted three times with THF (500–600 mL each). The latter combined organic extracts were dried over anhydrous magnesium sulfate, filtered, and concentrated in vacuo to provide 32.7 g (99.5 percent) of white solids. Proton nmr (Gemini model 300 MHz) in deuterochloroform: delta 8.08 (2H), 7.50 (2H), 6.78 (1H), 5.90 (1H), 5.41 (1H).

Example 4

Preparation of p-Carbomethoxycinnamic Acid.

To a 3-L three-necked round-bottom flask equipped with an overhead stirrer, condenser, and a nitrogen/thermocouple unit was added methyl p-formylbenzoate (82.08 g, 0.50 mole), malonic acid (104.06 g, 1.00 mole), and pyridine (200 mL). Stirring was started followed by heating to 50° C. for 75 minutes. By this time, a sizable amount of solids had formed and to this mixture was added piperidine (7.5 mL, 0.076 mole) and the temperature raised to 80° C. After another one hour at 80° C., the temperature was raised to 115° C. After another 2.5 hours at this temperature, heating was stopped and the mixture allowed to cool before pouring into water (2 L). To the aqueous mixture was carefully added concentrated HCI (250–300 mL) until the mixture became acidic. The mixture was filtered, and the solids washed with fresh water (1 L) before being suction dried. A yield of 96.83 g (93.9 percent) of white solids was obtained. Proton nmr (DMSO-d6) delta: 7.95 (2H, d); 7.80 (2H, d); 7.60 (1H, d); 6.62 (1H, d); 3.82 (3H, s).

Example 5

Preparation of Methyl p-vinylbenzoate (MVB) by Decarboxylation of p-carbomethoxycinnamic acid To a 300 mL, three-necked round-bottom flask equipped with an overhead stirrer, nitrogen/thermocouple unit, and a semi-circle shaped adapter with a round-bottom flask attached (to collect distillate) was added p-carbomethoxycinnamic acid (99.93 g, 0.485 mole) and copper powder (1.02 g). The mixture was heated to 258° C. for about 30 minutes while 5–10 mL of distillate was collected. The temperature was raised to 290° C. for 15–20 minutes while a small amount of additional distillate was collected. The mixture was allowed to cool slightly, then carefully poured into a 1-L flask containing a 4 to 1 mixture of hexanes to ethyl acetate (800 mL combined). Immediately, grayish-green solids formed upon addition and the mixture was filtered. Gas chromatography of the filtrate showed the mixture to be about 70 percent p-carbomethoxycinnamic acid and about 27 percent methyl p-vinylbenzoate. The solids were washed with fresh ethyl acetate, then filtered. This filtrate contained about 59 percent p-carbomethoxycinnamic acid and about 41 percent methyl p-vinylbenzoate. The distillate collected was diluted with ethyl acetate which caused two layers to form. Gas chromatography of the bottom layer showed a mixture of 37 percent p-carbomethoxycinnamic acid and 63 percent methyl p-vinylbenzoate. Gas chromatography of the top layer contained 10 percent p-carbomethoxy-cinnamic acid, 27 percent unidentified material, and 49 percent methyl p-vinylbenzoate.

Example 6

Latex Preparation—Comparative Example

This example illustrates the formation of a latex polymer using a commercially available, widely used methyl methacrylate monomer (MMA), by free radical polymerization.

To a 1 L jacketed reaction kettle equipped with a condenser, nitrogen purge, and stirrer, 150 g of water containing 5.0 g of Abex EP-100 surfactant was added. The contents of the reactor were heated to 70° C. In a separate flask, 100.0 g of MMA were weighed. In a separate container, 0.5 g of ammonium persulfate, used as an initiator, was dissolved in 50 g of distilled water. To the heated reactor, the monomer and initiator were pumped separately over a period of 2.0–3.0 hours. After a few minutes, the reactor appearance changed from clear to a bluish-white tint indicating the formation of small particles. The remaining monomer mixture and initiator were continuously fed into the reactor. After all the monomer mixture was added, the reaction was held at 70° C. for an additional hour at which point the reactor was cooled to room temperature.

The resulting latex was filtered through a multi-layered cheese-cloth. The latex was evaluated for solids content using a Computrac and an oven at 80° C. The latex contained 38.24% solids by Computrac and 38.58% solids by oven drying method. The Tg of the dried latex polymer was 130.13° C. Molecular weight (Mw) of the latex polymer was 1,586,253 and (Mn) was 8,768 with polydispersity of 180.9. The MMA polymer formation was confirmed by Proton NMR.

Average particles size of the latex dispersions, as measured by light scattering method, was 121.5 nm. The acid number of the acrylic copolymer was 7.5 mg/g.

Example 7

Latex Emulsion Polymerization (MMA/MVB)

This example illustrates the process of preparing acrylic latexes using methyl methacrylate (MMA) and methyl p-vinyl benzoate (MVB). The methyl p-vinyl benzoate used was from Example 1. 50 g of MVB was dissolved in 50 g of MMA monomer using mixing devices known in the art. To a 1 L jacketed reaction kettle equipped with a condenser, nitrogen purge, and stirrer, 150 g of water containing 5.0 g of Abex EP-100 surfactant was added. The contents of the reactor were heated to 70° C. In a separate 500 ml flask, a monomer mixture containing 50.0 g of MMA and 50.0 g of MVB was prepared. In a separate container, 0.5 g of ammonium persulfate, used as an initiator, was dissolved in 50 g of distilled water. To the heated reactor, the monomer mixture and initiator were pumped separately over a period of 2.0–3.0 hours. After a few minutes, the reactor appearance changed from clear to a bluish-white tint indicating the formation of small particles. The remaining monomer mixture and initiator were continuously fed into the reactor. After all the monomer mixture was added, the reaction was held at 70° C. for an additional hour at which point the reactor was cooled to room temperature.

The resulting latex was filtered through a multi-layered cheese-cloth. The latex was evaluated for solids content using a Computrac and an oven at 80° C. The latex contained 31.25% solids by Computrac and 31.88% solids by oven drying method. The Tg of the dried latex polymer was 126.1° C. Molecular weight (Mw) of the latex polymer was 1,136,646 and (Mn) was 41,299 with polydispersity of 27.522. The MMA/MVB copolymer formation was also confirmed by Proton NMR.

Average particles size of the latex dispersions as measured by light microscopy was 110.3 nm. The acid number of the acrylic copolymer was 1.7 mg/g.

Example 8

Latex Emulsion Polymerization (BA/MVB)

Example 7 was repeated with the exception that butyl acrylate (BA) monomer was used instead of MMA monomer in preparing latexes.

The resulting latex was filtered through a multi-layered cheese-cloth. The latex was evaluated for solids content using a Computrac and an oven at 80.0° C. The material contained 29.54% solids by Computrac and 30.52% solids by oven drying method. The Tg of the dried latex polymer was 58.54° C. Molecular weight (Mw) of the latex polymer was 1,197,992 and (Mn) was 270,130 with polydispersity of 4.435. The BA/MVB copolymer formation was also confirmed by Proton NMR.

Average particles size of the latex dispersions as measured by light microscopy was 63.0 nm. The acid number of the acrylic copolymer was 1.07 mg/g.

Example 9

Latex Emulsion Polymerization (BA/MVB)

Example 8 was repeated under identical conditions for determining the reproducibility of the process and properties of the acrylic latexes.

The resulting latex was filtered through a multi-layered cheese-cloth. The latex was evaluated for solids content using a Computrac and an oven at 80.0° C. The material contained 32.98% solids by Computrac and 33.8% solids by oven drying method. The Tg of the dried latex polymer was 57.11° C. Molecular weight (Mw) of the latex polymer was 1,609,284 and (Mn) was 356,346 with polydispersity of 4.516. The BA/MVB copolymer formation was also confirmed by Proton NMR.

Average particles size of the latex dispersions as measured by light microscopy was 76.9 nm. The acid number of the acrylic copolymer was 1.34 mg/g.

Example 10

Latex Emulsion Polymerization (VBA/Styrene/2-HEMA)

This example illustrates the process of preparing acrylic latexes using p-vinyl benzoic acid (VBA). The p-vinyl benzoic acid used was from Example 3. The VBA (5.0 g) was dissolved in 50/50 ratio of styrene and 2-hydroxyethyl methacrylate (2-HEMA) monomer mixture using mixing devices known in the art. To a 1 L jacketed reaction kettle equipped with a condenser, nitrogen purge, and stirrer, 150 g of water containing 5.0 g of Abex EP-100 surfactant was added. The contents of the reactor were heated to 70° C. In a separate 500 ml flask, a monomer mixture containing 47.5 g of styrene, 47.5 g of 2-HEMA and 5.0 g of VBA was prepared. In a separate container, 0.5 g of ammonium persulfate, used as an initiator, was dissolved in 50 g of distilled water. To the heated reactor, the monomer mixture and initiator were pumped separately over a period of 2.0–3.0 hours. After a few minutes, the reactor appearance changed from clear to a bluish-white tint indicating the formation of small particles. The remaining monomer mixture and initiator were continuously fed into the reactor. After all the monomer mixture was added, the reaction was held at 70° C. for an additional hour at which point the reactor was cooled to room temperature.

The resulting latex was filtered through a multi-layered cheese-cloth. The latex was evaluated for solids content using a Computrac and an oven at 80° C. The latex contained 35.26% solids by Computrac and 36.05% solids by oven drying method. The Tg of the dried latex polymer was 116.57° C. Molecular weight (Mw) of the latex polymer was 213,807 and (Mn) was 1,395 with polydispersity of 165.71. The material did not dissolve completely in the solvents for analysis indicating the cross-linking of the functional group in the latex polymer.

Average particles size of the latex dispersions as measured by light microscopy was 141.5 nm. The acid number of the acrylic copolymer was 5.27 mg/g and hydroxyl number was 193.36.

Example 11

Latex Emulsion Polymerization (VBA/Styrene/2-HEMA)

Example 10 was repeated with the exception that the latexes were dried at room temperature instead of 80° C.

Molecular weight (Mw) of the latex polymer was 589,548 and (Mn) was 53,792 with polydispersity of 10.96. The number average molecular weight of the acrylic polymer is higher for the air dried sample as compared to the same latex dried at 80° C., indicating low polydispersity of the latex polymer.

Example 12

Latex Emulsion Polymerization (VBA/Styrene/2-HEMA)

Example 10 was repeated with the exception that different amounts of styrene, 2-HEMA and VBA monomers were used in the latex formation. The p-vinyl benzoic acid used was from Example 3. The VBA (2.5 g) was dissolved in styrene and 2-hydroxyethyl methacrylate (2-HEMA) monomer mixture using mixing devices known in the art. To a 1 L jacketed reaction kettle equipped with a condenser, nitrogen purge, and stirrer, 150 g of water containing 5.0 g of Abex EP-100 surfactant was added. The contents of the reactor were heated to 70° C. In a separate 500 ml flask, a monomer mixture containing 95.0 g of styrene, 2.5 g of 2-HEMA and 2.5 g of VBA was prepared. In a separate container, 0.5 g of ammonium persulfate, used as an initiator, was dissolved in 50 g of distilled water. To the heated reactor, the monomer mixture and initiator were pumped separately over a period of 2.0–3.0 hours. After a few minutes, the reactor appearance changed from clear to a bluish-white tint indicating the formation of small particles. The remaining monomer mixture and initiator were continuously fed into the reactor. After all the monomer mixture was added, the reaction was held at 70° C. for an additional hour at which point the reactor was cooled to room temperature.

The resulting latex was filtered through a multi-layered cheese-cloth. The latex was evaluated for solids content using a Computrac and an oven at 80° C. The latex contained 34.25% solids by Computrac and 34.50% solids by oven drying method. The Tg of the dried latex polymer was 114.78° C. Molecular weight (Mw) of the latex polymer was 1,247,729 and (Mn) was 3,628 with polydispersity of 343.90. The material did not dissolve completely in the solvents for analysis indicating the cross-linking of the functional group in the latex polymer. Average particles size of the latex dispersions as measured by light microscopy was 81.0 nm. The acid number of the acrylic copolymer was 3.98 mg/g and hydroxyl number was 20.67.

Example 3

Latex Emulsion Polymerization (VBA/Styrene/2-HEMA)

Example 12 was repeated with the exception that the latexes were dried at room temperature instead of 80° C.

Molecular weight (Mw) of the latex polymer was 1,064,073 and (Mn) was 112,616 with polydispersity of 9.45. The number average molecular weight of the acrylic polymer is higher for the air dried sample as compared to the same latex dried at 80° C., indicating low polydispersity of the latex polymer.

In the specification, there has been disclosed typical preferred embodiments of the invention and, although specific terms are employed, they are used in a generic and descriptive sense only and not for purposes of limitation, the scope of the invention being set forth in the following claims.

What is claimed is:

1. A process for the preparation of methyl p-vinylbenzoate comprising reacting methyl p-formylbenzoate and ketene in the presence of a potassium salt to form methyl p-vinylbenzoate.

2. The process of claim 1 wherein the potassium salt is selected from the group consisting of potassium acetate, potassium carbonate, potassium benzoate, potassium cinnamate, and potassium proprionate.

3. The process of claim 1 wherein the molar ratio of potassium salt to methyl p-formylbenzoate is less than 0.50.

4. The process of claim 1 wherein the molar ratio of potassium salt to methyl p-formylbenzoate is less than 0.20.

5. The process of claim 1 wherein the source of ketene is selected from the group consisting of acetone, diketene, acetic anhydride, and acetic acid.

6. The process of claim 1 further comprising the addition of a solvent.

7. The process of claim 6 wherein the solvent is selected from the group consisting of aliphatic and cycloaliphatic hydrocarbons; aromatic hydrocarbons; cyclic and acyclic ethers, esters and ketones.

8. A process for the preparation of p-carbomethoxycinnamic acid comprising reacting methyl p-formylbenzoate and ketene in the presence of a potassium salt to form p-carbomethoxycinnamic acid.

9. The process of claim 8 wherein the potassium salt is selected from the group consisting of potassium acetate, potassium carbonate, potassium benzoate, potassium cinnamate, and potassium proprionate.

10. The process of claim 8 wherein the molar ratio of potassium salt to methyl p-formylbenzoate is less than 0.50.

11. The process of claim 8 wherein the molar ratio of potassium salt to methyl p-formylbenzoate is less than 0.20.

12. The process of claim 8 wherein the source of ketene is selected from the group consisting of acetone, diketene, acetic anhydride, and acetic acid.

13. The process of claim 8 further comprising the addition of a solvent.

14. The process of claim 13 wherein the solvent is selected from the group consisting of aliphatic and cycloaliphatic hydrocarbons; aromatic hydrocarbons; cyclic and acyclic ethers, esters and ketones.

* * * * *